(12) United States Patent
Satasiya et al.

(10) Patent No.: US 9,308,104 B2
(45) Date of Patent: Apr. 12, 2016

(54) STENT REMOVAL AND REPOSITIONING DEVICE AND ASSOCIATED METHOD

(75) Inventors: Pankaj Satasiya, Charlotte, NC (US); Tony Alexander, Charlotte, NC (US)

(73) Assignee: Merit Medical Systems, Inc., South Jordon, UT (US)

( * ) Notice: Subject to any disclaimer, the term of this patent is extended or adjusted under 35 U.S.C. 154(b) by 1783 days.

(21) Appl. No.: 11/577,858

(22) PCT Filed: Oct. 24, 2005

(86) PCT No.: PCT/US2005/038382
§ 371 (c)(1),
(2), (4) Date: Jan. 11, 2008

(87) PCT Pub. No.: WO2006/047520
PCT Pub. Date: May 4, 2006

(65) Prior Publication Data
US 2008/0243225 A1 Oct. 2, 2008

Related U.S. Application Data

(60) Provisional application No. 60/621,816, filed on Oct. 25, 2004.

(51) Int. Cl.
*A61F 2/06* (2013.01)
*A61F 2/95* (2013.01)
(Continued)

(52) U.S. Cl.
CPC ... *A61F 2/95* (2013.01); *A61F 2/91* (2013.01); *A61F 2/915* (2013.01); *A61F 2002/075* (2013.01); *A61F 2002/91533* (2013.01);
(Continued)

(58) Field of Classification Search
CPC ... A61F 2/95; A61F 2/962; A61F 2002/9534; A61F 2002/9528
USPC ......... 606/108, 113, 127, 128, 200; 623/1.11, 623/1.15, 1.12
See application file for complete search history.

(56) References Cited

U.S. PATENT DOCUMENTS 4,273,131 A * 6/1981 Olsen ............................ 606/191
5,474,563 A * 12/1995 Myler et al. ................... 606/108
(Continued)

FOREIGN PATENT DOCUMENTS

WO      WO 00/44308 A2      8/2000

OTHER PUBLICATIONS

International Search Report for PCT/US2005/038382, completed on Feb. 23, 2006.
Written Opinion for PCT/US2005/038382, dated May 10, 2007.

*Primary Examiner* — Gregory Anderson
*Assistant Examiner* — Christina Lauer
(74) *Attorney, Agent, or Firm* — Stoel Rives LLP

(57) ABSTRACT

A stent removal device for removing or repositioning a stent from within a lumen is provided. The stent typically comprises at least one element arranged circumferentially about the stent. The stent removal device includes a tube positioned within the lumen proximate to the stent, wherein the tube is capable of receiving at least a portion of the stent. The stent removal device also includes a pusher positioned within the tube capable of engaging the stent and/or the element. The stent removal device further includes a hook positioned within the tube and including a hook member capable of engaging the element such that force applied to the hook causes the stent to purse string.

20 Claims, 8 Drawing Sheets

(51) Int. Cl.
*A61F 2/91* (2013.01)
*A61F 2/915* (2013.01)
*A61F 2/07* (2013.01)

(52) U.S. Cl.
CPC ............... *A61F2002/91575* (2013.01); *A61F 2002/9511* (2013.01); *A61F 2002/9528* (2013.01); *A61F 2220/0075* (2013.01); *A61F 2230/0054* (2013.01)

(56) References Cited

U.S. PATENT DOCUMENTS

| | | | | |
|---|---|---|---|---|
| 5,910,144 | A | * | 6/1999 | Hayashi ........................ 606/108 |
| 6,165,209 | A | * | 12/2000 | Patterson et al. .............. 623/1.1 |
| 2002/0120277 | A1 | * | 8/2002 | Hauschild et al. ............ 606/108 |
| 2002/0188344 | A1 | * | 12/2002 | Bolea et al. .................. 623/1.11 |

* cited by examiner

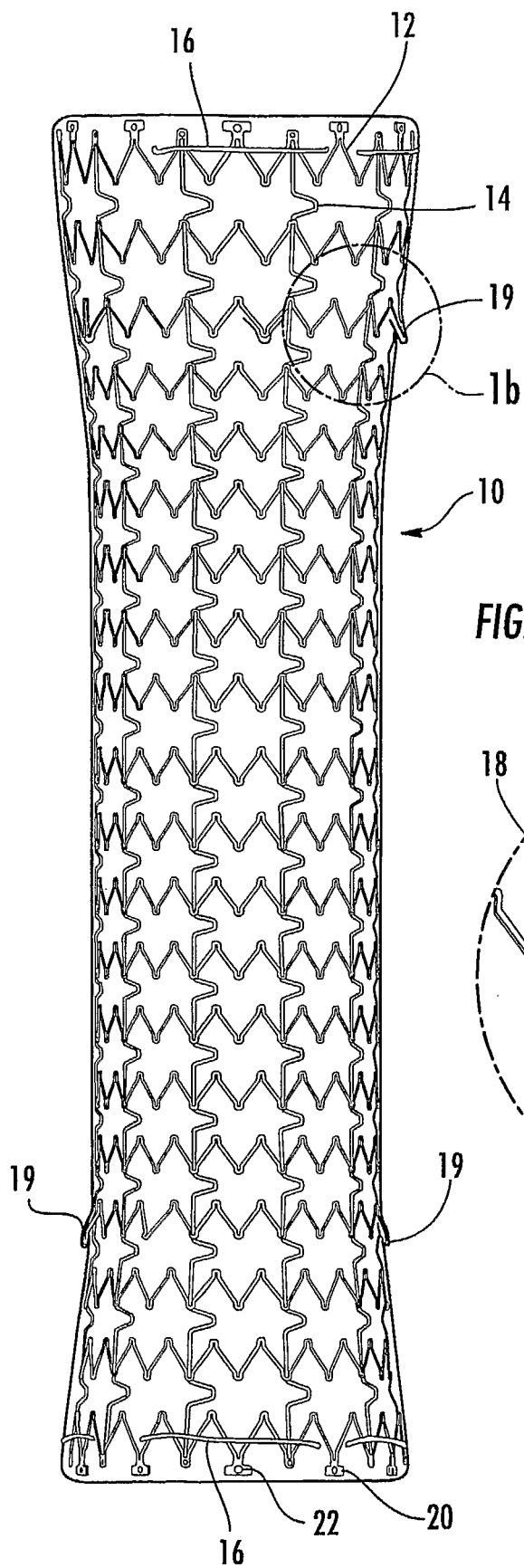
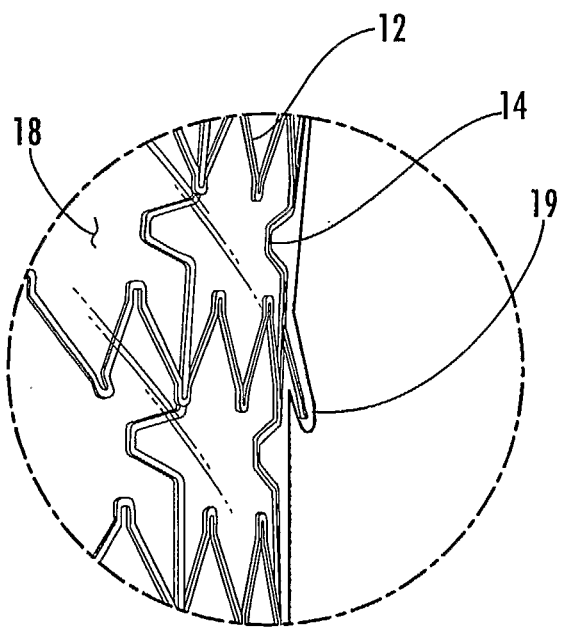
FIG. 1a
FIG. 1b

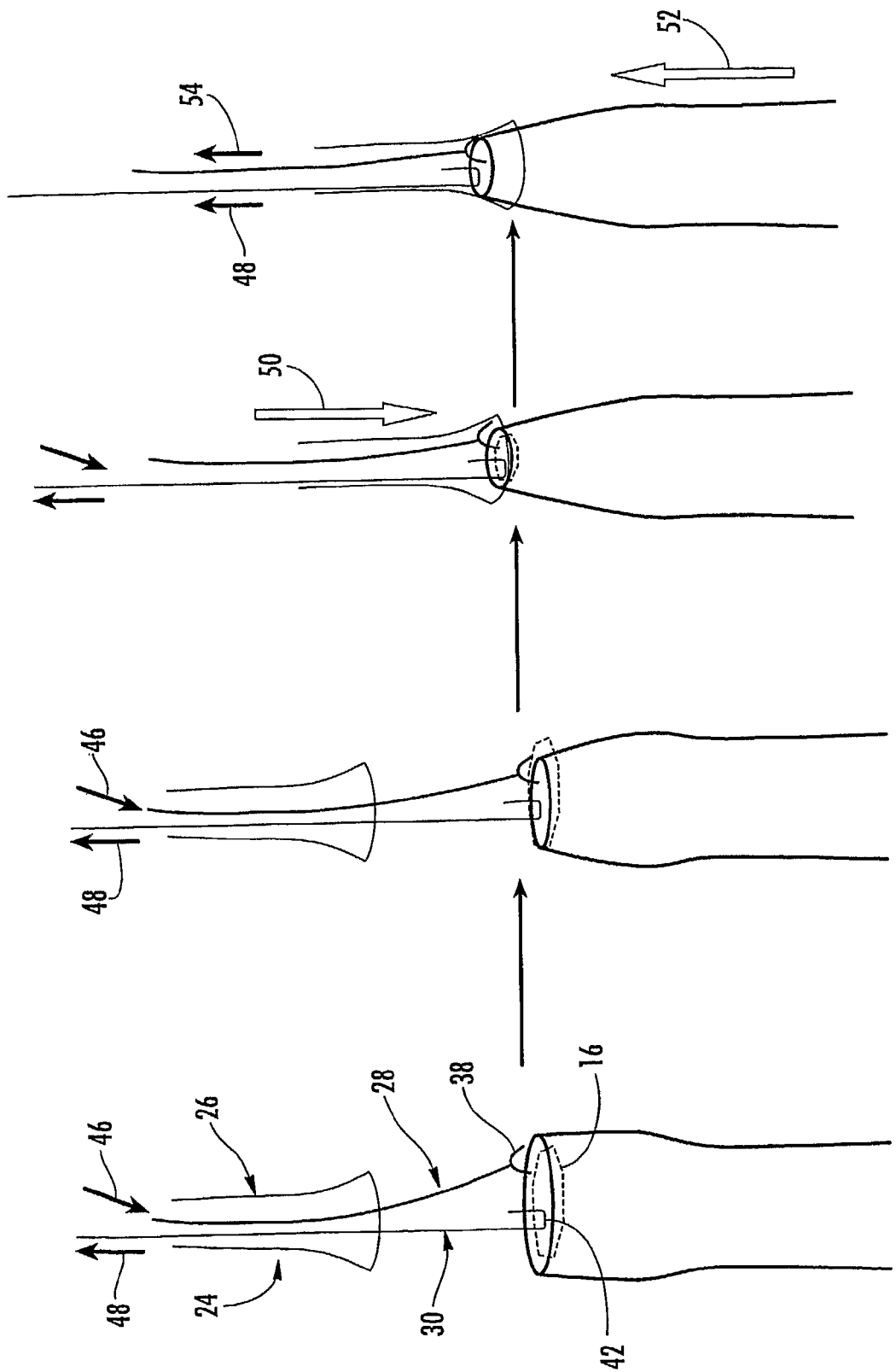

STENT REMOVAL AND REPOSITIONING DEVICE AND ASSOCIATED METHOD

BACKGROUND OF THE INVENTION

1) Field of the Invention

The present invention relates to a stent device and, in particular, to a stent removal and repositioning device that is capable of removing a stent from a lumen or repositioning the stent within the lumen.

2) Description of Related Art

Stents are devices that are inserted into body lumens such as vessels or passages to keep the lumen open and prevent closure due to a stricture, external compression, or internal obstruction. In particular, stents are commonly used to keep blood vessels open in the coronary arteries, and they are frequently inserted into the ureters to maintain drainage from the kidneys, the bile duct for pancreatic cancer or cholangiocarcinoma, or the esophagus for strictures or cancer. Vascular as well as nonvascular stenting has evolved significantly; unfortunately, there remain significant limitations with respect to the technology for positioning and removing stents following implantation into various portions of a patient's anatomy.

In various areas of application, e.g., bronchus, biliary, trachea, or esophagus, the stents must be removable from the body or repositionable as a function of the course of the disease or treatment. This can be problematic since newly formed tissue can grow on the support frame of the stent and even grow through it, which can result in complications when removing a stent. In this regard, stents have been developed that include a support frame surrounded on the outside by a thread or wire. The support frame can be radially constricted by pulling on the thread ends that are each provided with a loop or the like, creating a "purse-string" effect, which makes it possible for the frame to be removed. However, when the wire or thread is guided or braided in multiple windings around the support frame, a high degree of friction results between the two stent components, which has a disadvantageous effect on the explantation process. In addition, stents having eyelets for looping the thread therethrough may have sharp edges that cause the thread to tear or break during the removal process.

Alternatively, surgeons have grasped the stent with forceps or a similar instrument to reposition or remove the stent from within the lumen. However, this can be complex at times. For instance, grasping the stent risks damage to the stent and/or the surrounding tissue, e.g., during removal of a tracheal stent with grasping forceps, the vocal chords may be damaged if the stent is in its deployed state with an expanded diameter. Also, grasping may lead to damage to the stent itself, as the forceps may have difficulty accessing or adequately gripping the stent to remove or reposition it.

Thus, there is a need in the industry for a stent removal device that reduces the risk of damage to the stent, thread or suture, and the surrounding tissue. In addition, there is a need for a stent removal device that is capable of easily accessing the stent, as well as effectively constricting the stent and thereafter repositioning and/or removing the stent from a lumen.

BRIEF DESCRIPTION OF THE SEVERAL VIEWS OF THE DRAWINGS

Figure 2:
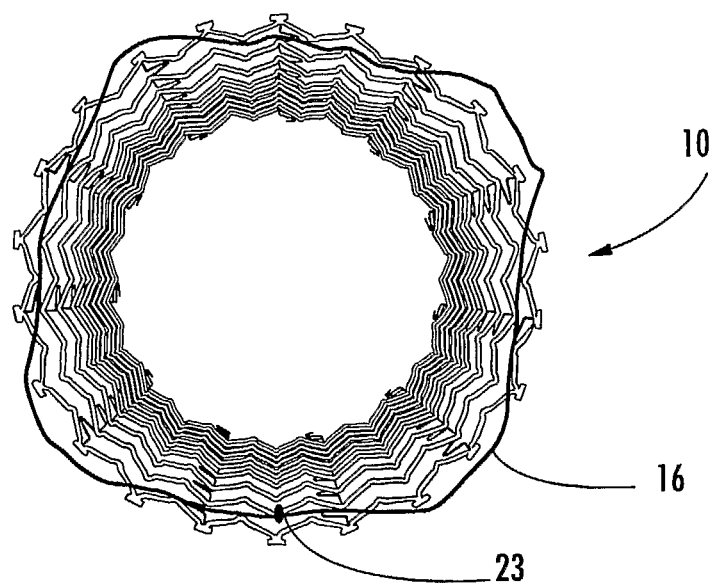
Figure 3:
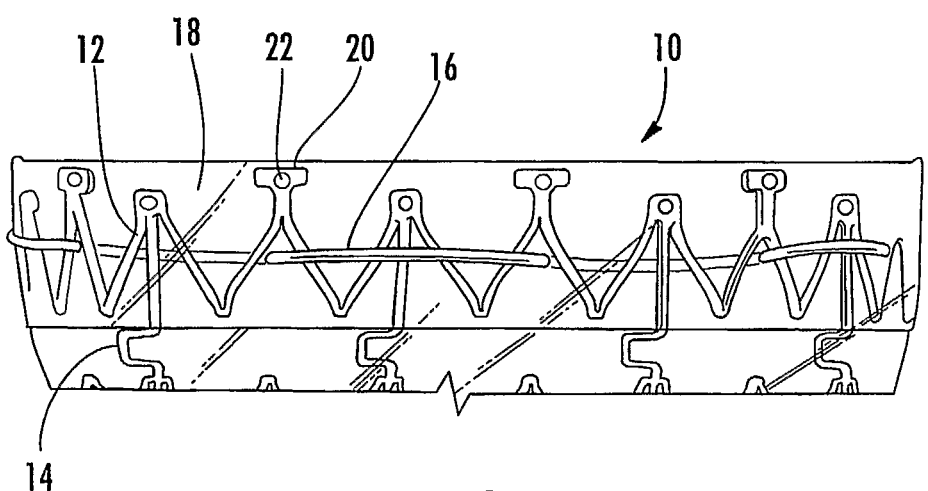
Figure 4:
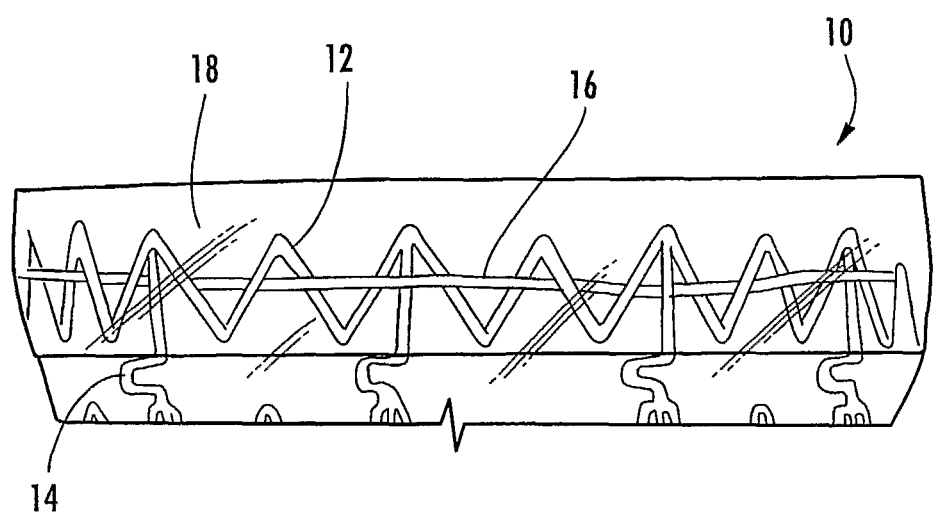
Figure 5:
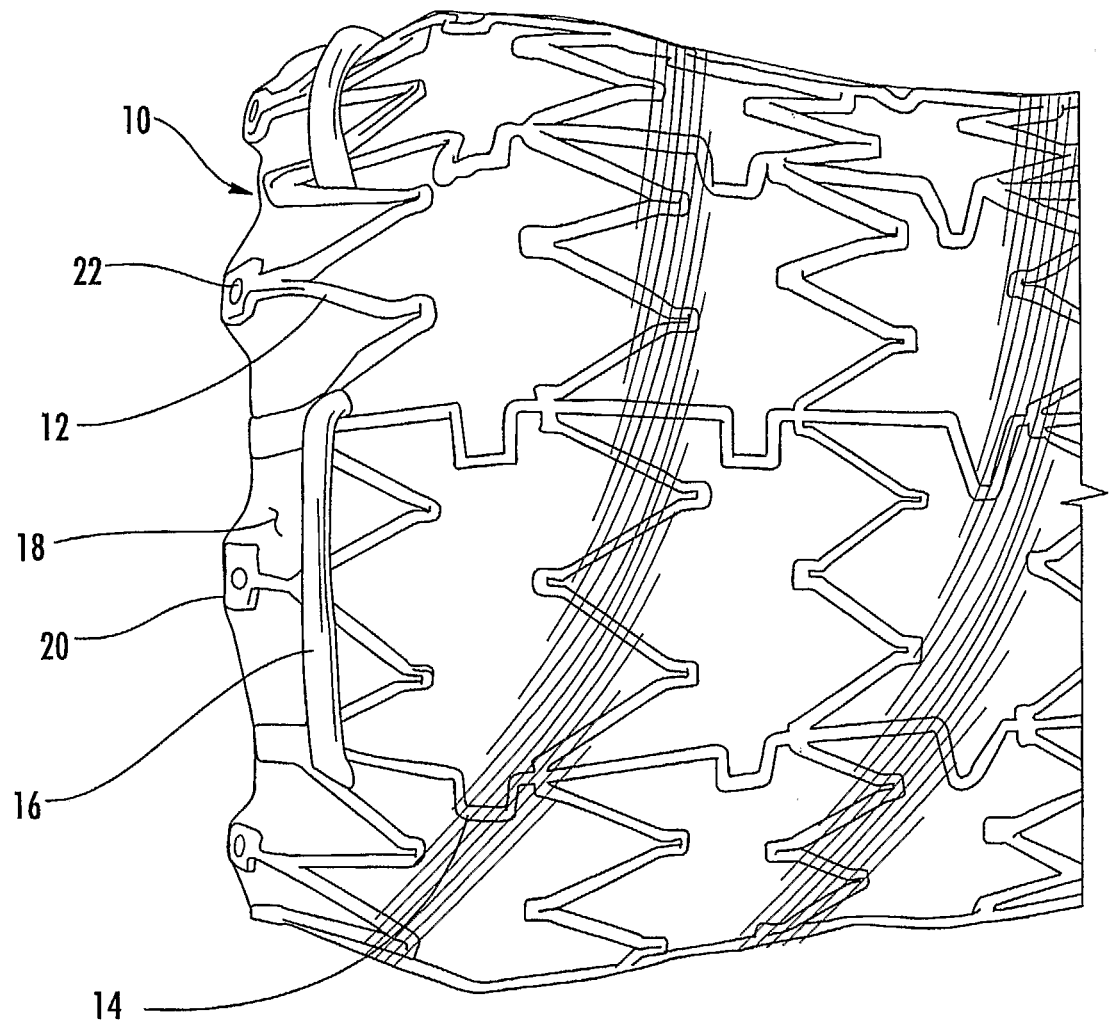
Figure 6:
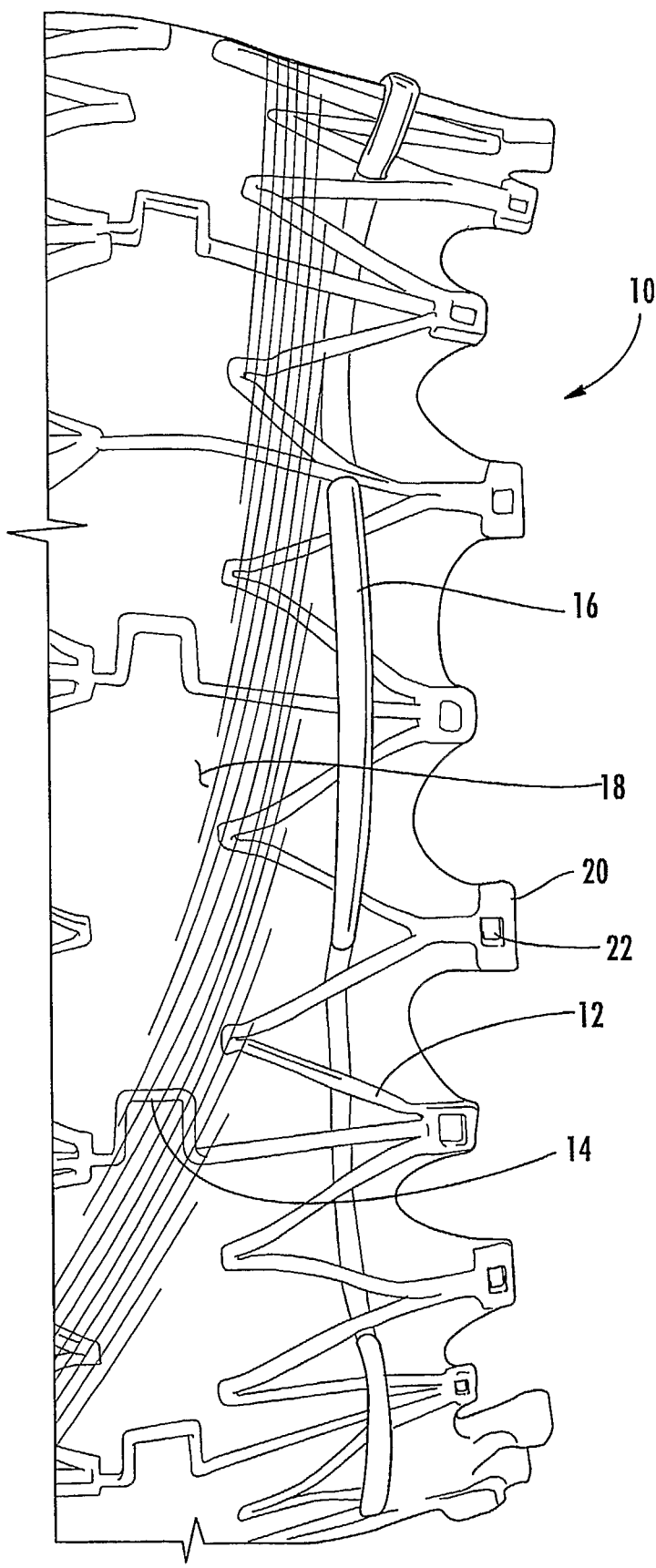
Figures 7, 7A:
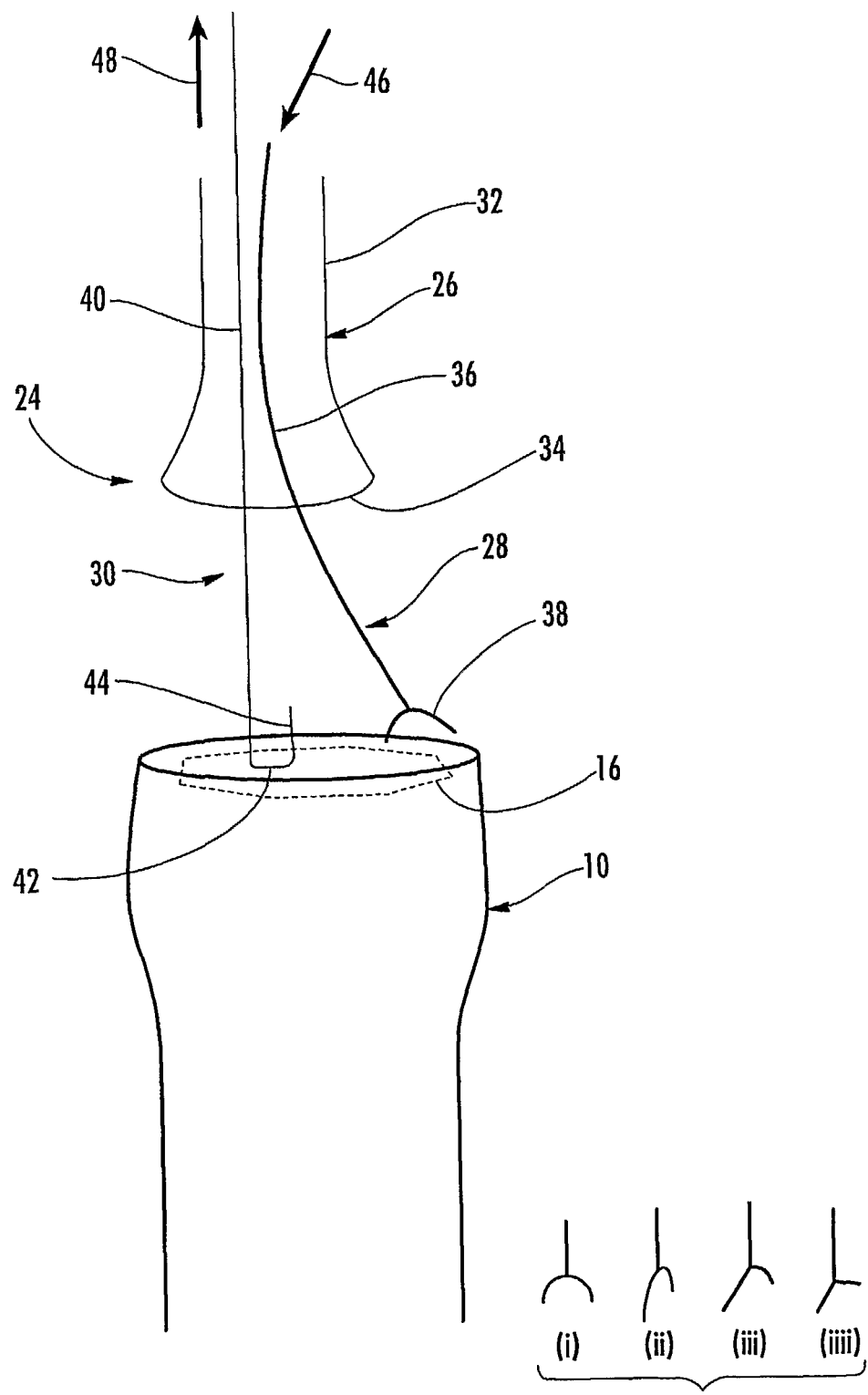
Figure 8:
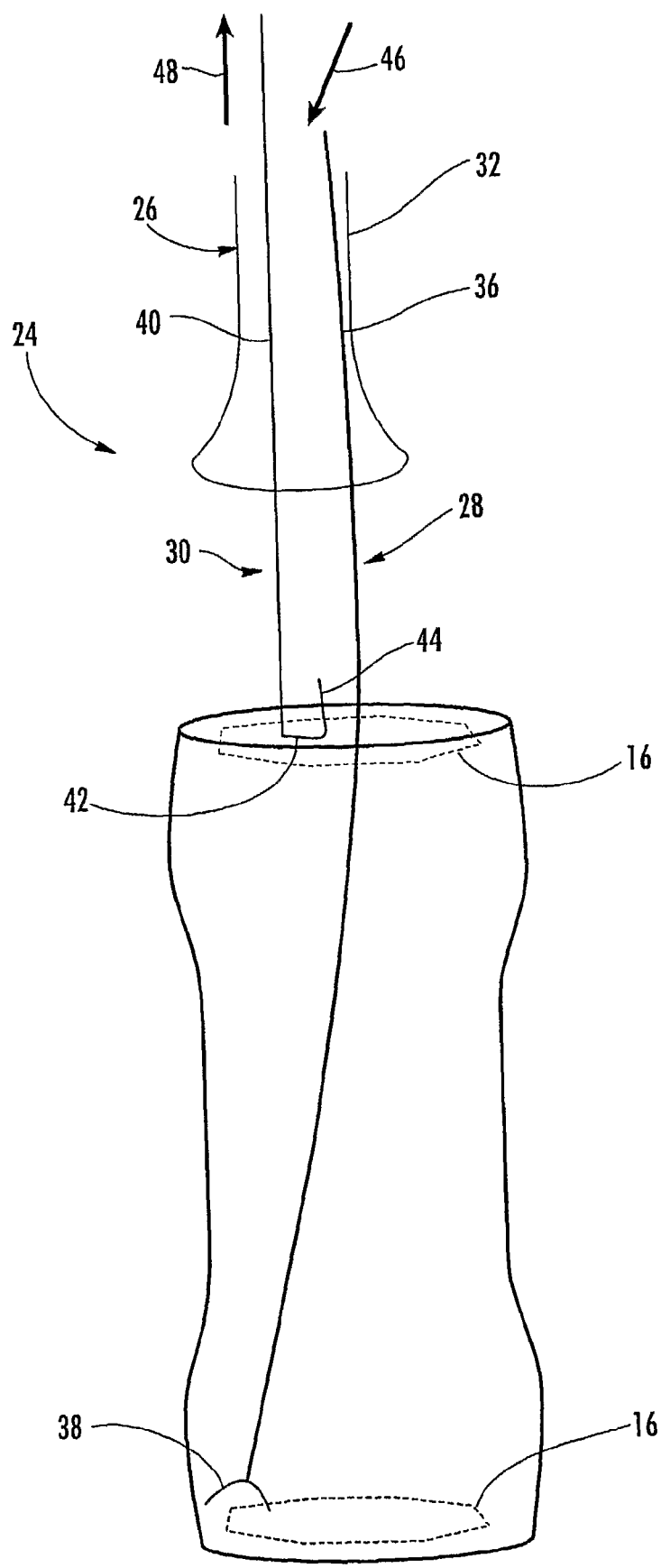

Having thus described the invention in general terms, reference will now be made to the accompanying drawings, which are not necessarily drawn to scale, and wherein:

FIG. 1a is a plan view of a stent having an interstice geometry, according to one embodiment of the present invention;

FIG. 1b is an enlarged view of a portion of the stent shown in FIG. 1a, further illustrating the interstice geometry;

FIG. 2 is an end view of the stent shown in FIG. 1a, depicting a suture arranged circumferentially about the stent, according to one embodiment of the present invention;

FIG. 3 is an enlarged view of a portion of the stent as seen in FIG. 1a and illustrating the suture arranged throughout interstices of the stent;

FIG. 4 is an enlarged view of a portion of a stent having a suture arranged thereabout, according to an additional embodiment of the present invention;

FIG. 5 is an enlarged view of a stent illustrating a suture arranged throughout the interstices of the stent according the invention;

FIG. 6 is a greatly enlarged view of a threaded suture arranged about a stent according to the invention;

FIG. 7 is a perspective view illustrating a stent removal device, according to one embodiment of the present invention;

FIG. 7a depicts enlarged views of various configuration of a gripping member capable of being employed with the stent removal device shown in FIG. 7;

FIG. 8 is a perspective view illustrating a stent removal device, according to an additional embodiment of the present invention; and FIGS. 9a-d illustrate a series of perspective views demonstrating a sequence of steps to remove or reposition a stent with the stent removal device of FIG. 7.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

With reference to FIGS. 1-3, a stent 10 is shown having interstice geometry. The stent 10 includes a scaffolding of struts, as well as a suture 16 intertwined about the struts. The struts generally include a plurality of interconnected legs 12 and connectors 14. As shown in FIG. 1a, the stent 10 includes a series of legs 12 arranged circumferentially about the stent, as well as arranged in a series of rows along the longitudinal axis of the stent, while a plurality of connectors 14 are arranged parallel to the longitudinal axis of the stent to connect the rows together. The suture 16 is preferably located proximate to each of the proximal and distal ends of the stent 10, as shown in FIG. 1a. FIG. 1b demonstrates that there is a cover 18 layer extending between the legs 12 and connectors 16.

The legs 12 and connectors 14 of the stent 10 are preferably formed from a composite material such as Ni, C, Co, Cu, Cr, H, Fe, Nb, O, Ti and combinations thereof (e.g., Nitinol). The composite material is generally formed into a compressed tube from which the stent is etched and is formed on a suitable shaping device to give the stent the desired external geometry. The stent 10 is formed of a memory metal that facilitates flexibility of the stent 10 such that the stent may be deformed and return to its original shape.

The stent 10 is generally cylindrical, having openings at the proximal and distal ends. As illustrated in FIG. 1a, the diameter of the proximal and distal ends is slightly larger than the diameter of longitudinal portion of the stent extending therebetween. In the event the stent 10 is to be shaped to the dimensions of a particular lumen, optical photography and/or optical videography of the target lumen may be conducted prior to stent formation. The interstice geometry of the stent 10 then can be etched and formed in accordance with the requirements of that target lumen. For example, if the stent 10 were designed for the trachea, which has a substantially D shaped lumen and additionally the middle portion of the stent is preferably softer than the proximal or distal ends, the stent could be designed to those specifications. In particular, if the topography of the trachea of a particular patient is captured optically and the appropriate dimension provided, a patient specific prosthesis could be engineered. These techniques can be adapted to other non-vascular lumina but is very well suited for vascular applications where patient specific topography is a function of a variety of factors such as genetics, lifestyle, etc.

It should be pointed out that, unlike the use of differing shape memory materials to change regions of a stent 10, stents in accordance with the present invention can take on an infinite number of characteristic combinations of interstice geometry by changing angles, segment lengths, and segment thicknesses during the etching and forming stages of stent engineering or during post formation processing and polishing steps. Moreover, by modifying the geometry of the connectors 14, additional functionality may be achieved.

The cover 18 is typically a polymer, such as polyurethanes (e.g., polycarbonate urethane, or Chronoflex® manufactured by Cardiotech International), that is applied between the legs 12 and connectors 14 to provide a predetermined shape for the stent 10, as well as graft each of the legs and connectors into a unitary structure. The cover 18 typically does not inhibit flexing or radial expansion of the stent 10. However, it is possible to make the cover 18 affect the flexing and radial expansion of the stent 10. The cover 18 typically forms a thin film when deposited on the stent 10.

As shown in FIGS. 5-6, the interstices are raised above the surface of the cover 18. Thus, the cover 18 is preferably applied to the interior of the stent 10 such that the stent scaffolding is raised above the surface of cover (e.g., 1 Å to $10^6$ Å). Providing a raised scaffolding above the surface of the cover 18 promotes cilia action by allowing cilia movement between stent 10 struts. However, as shown in FIG. 1b, the cover 18 may be applied to the exterior of the stent 10 scaffolding, or may even be on applied on both sides of the scaffolding.

FIG. 1b also illustrates a scale 19 extending outwardly from the outer surface of the stent 10. The scale 19 is generally one or more legs 12 that protrude in a manner that act to prevent migration of the stent 10 when implanted into the lumen. For example, the scale 19 depicted in FIG. 1b would prevent migration of the stent 10 in a downward direction. The scales 10 may extend from the outer surface in any number of orientations, and the scales typically 19 define an acute angle between the protruding leg(s) and the outer surface of the stent 10, although various angles may be incorporated in additional embodiments of the present invention. The scales 19 may extend from the outer surface of the stent 10 in any desired location and as shown in FIG. 1, for example, the scales are located in the third or fourth row of legs 12. FIG. 1 also demonstrates that there may be several scales 19, although there may be any number of scales depending on the amount of anti-migration desired.

FIG. 3 illustrates that when the cover 18 is applied to the interior of the stent 10 scaffolding, the cover may fold back over on itself at the proximal and/or distal ends of the stent. The cover 18 in FIG. 3 is shown as folding back over a first row of legs 12 circumferentially about the stent 10, although the cover could fold back various amounts, such as along the ends 10 of the legs proximate to the proximal and/or distal ends of the stent, along several rows of legs and/or connectors 14, or not at all. Folding the cover 18 ensures that the proximal and distal ends of the stent 10 are smooth. In addition, folding the cover 18 prevents the ends 20 of the legs 12 from interlocking with one another during manufacturing or manipulation of the stent 10. For instance, the stent 10 shown in FIG. 3 includes T-shaped ends 20 that could potentially interlock with legs 12 and/or connectors 14 when the stent is folded or compressed.

The suture 16 may be any suitable suture material, as known to those skilled in the art, such as polypropylene. However, it is understood that the term "suture" as used herein could be any suitable thread or wire, as known to those skilled in the art, capable of enduring the forces applied during repositioning or removal of the stent 10 in alternative embodiments of the present invention.

Any number of configurations of stents 10 could be incorporated and still be within the present scope of the invention. An exemplary embodiment of the interstice geometry of a stent 10 and methods of manufacturing the stent is disclosed in U.S. Patent Publication No. 20040127973 (application Ser. No. 10/674,972), entitled "Removable Biliary Stent," which is assigned to the present assignee and is incorporated herein by reference. Thus, the interstice geometry of the stent 10 should not be limited to that depicted in the disclosed Figures, as any number of configurations of interstice geometry could be employed with the present invention to achieve various degrees of rigidity and functionality. U.S. Patent Publication No. 20040122511 (application Ser. No. 10/669,450) entitled "Coated Stent with Geometry Determined Functionality and Method of Making the Same," which is assigned to the present assignee, is also incorporated herein by reference, and further describes the cover 18 that may be employed with the present invention, including the types of materials and properties suitable for the cover, as well as the process of manufacturing the stent 10.

As depicted in FIG. 3, the suture 16 typically extends through the cover 18, along a series of legs 12, and then exits out of the cover. The intertwining of the suture 16 through the cover 18 and along the legs 12 continues about the entire circumference of the stent 10 until the ends of the suture are joined together such as with a knot 23, as shown in FIG. 2. The suture 16 in FIG. 2 is shown as being loosely arranged about the circumference of the stent 10 for illustrative purposes only, as the suture will typically be in more intimate contact with the stent. However, the suture 16 typically provides a minimal radial restraining force, if any force at all, and does not affect the shape of the stent 10, as the suture lies generally flush with the surface of the stent. In addition, the suture 16 is arranged about the circumference of the stent 10 such that the suture is accessible by a hook 30, which will be described in greater detail below.

The suture 16 is typically threaded along the circumference of the stent 10 proximate to the openings of the stent at the proximal and distal ends, and as shown in FIGS. 5-6, the suture is arranged along a first row of legs 12. In the embodiment depicted by the Figures, the suture 16 extends between two legs 12, across a plurality of legs, and then through another set of legs; however, the suture may be intertwined throughout the legs in any number of configurations. FIG. 2 demonstrates that the suture 16 is arranged about the entire circumference of the stent 10 such that the suture may produce a drawstring purse-string effect when pulled on by forceps or a similar instrument. In this regard, the purse-string effect acts against the outward radial force of the stent, and thus, the diameter of the stent is crimped or reduced.

FIG. 3 illustrates that the stent 10 may include ends 20 having apertures 22 defined therein through which the suture 16 may be threaded in order to purse string the stent. However, as depicted in FIG. 4, the stent 10 may also include legs 12 without apertures 22 such that the suture 16 is threaded along the legs 12 as described above. Therefore, the manner in which the suture 16 is arranged about the stent 10 to reduce the outward radial force of the stent is not limited to any specific configuration, as any suitable configuration for causing a purse-string effect on the proximal and/or distal ends of the stent may be employed with the present invention. Furthermore, it is understood that the suture 16 could be arranged in any number of configurations about the circumference of the stent 10 and could be located proximate to one or both ends of the stent.

FIG. 7 illustrates a stent removal device 24 that includes a tube 26, a pusher 28, and a hook 30. The tube 26 includes a cylindrical body 32 and a funnel-shaped end 34. The cylindrical body 32 is capable of accommodating the pusher 28 and the hook 30 such that the pusher and hook may be moved longitudinally within the cylindrical body and positioned on the stent 10. The funnel-shaped end 34 of the tube 36 is capable of receiving at least a portion of the stent 10 when the stent is crimped or constricted, as well as retaining the stent such that the tube may easily reposition or remove the stent from the lumen. The slope of the funnel-shaped end 34 of the tube 36 is angled such that the proximal end of the stent 10 may be readily pulled into the tube. It is understood that the funnel-shaped end 36 could be various configurations in additional embodiments of the present invention, such as a sloped, flared, angled, or similar configuration that is capable of accommodating a respective stent 10. Also for some configurations, the tube 26 need not have any type of enlarged distal end. Moreover, the inner wall of the tube 26 is preferably a low-friction surface to promote movement of the pusher 28 and hook 30 within the tube, as well as receive the proximal end of the stent 10.

The pusher 28 is typically a wire (e.g., stainless steel) that includes a longitudinal portion 36 positioned within the tube 26 and a gripping member 38. The gripping member 38 is capable of engaging an edge of the stent 10 to restrain the stent at its proximal end. Because the pusher 28 is employed to hold the stent 10 in place for subsequent repositioning or removal, the pusher is preferably a rigid wire that is capable of maintaining its shape while restraining the stent, but also having flexibility to be adaptable for a variety of vascular and nonvascular applications. In addition, the gripping member 38 includes a Y-shaped end that extends on either side of the edge of the stent 10. However, FIG. 7a demonstrates that the gripping member 38 may include various configurations that are capable of engaging the stent 10. Thus, the gripping member 38 could be U-shaped, Y-shaped, or asymmetrically U, Y, or L-shaped. In this regard, any suitable configuration of the gripping member 38 may be employed with the present invention that is capable of engaging and restraining the stent 10. Depending on the amount of force applied, the pusher 28 may cause slight distortion of the stent 10 adjacent to the application of force. However, because the stent 10 includes memory material, the stent will return to its original shape when the pusher removes the force.

Furthermore, FIG. 8 illustrates that the pusher 28 may be positioned through the stent 10 such that the gripping member 38 engages the suture 16 located proximate to the distal end of the stent. As such, the pusher 28 may be various lengths such that the gripping member may engage either a proximal end of the stent 10 or a suture 16 at the distal end of the stent. Similarly, the longitudinal portion 36 of the pusher 28 may be slightly curvilinear, as depicted in FIGS. 7 and 8, or may be substantially linear in alternative embodiments.

The hook 30 is also typically a wire (e.g., stainless steel) that includes a longitudinal portion 40 extending within the tube 26. The hook 30 further includes a hook member 42 that is capable of partially encircling the suture 16 such that pulling on the hook member causes the suture to purse string and crimp the end of the stent 10. The stent 10 is flexible, which allows the hook member 42 to access and engage the suture 16 without damaging the stent, suture, and/or lumen. The hook member 42 includes a ridge 44 that secures the suture 16 to prevent the suture from sliding or becoming disengaged by the hook member. The configuration and/or orientation of the hook member 42 is not limited to that depicted in FIGS. 7 and 8, as any suitable hook, snare, claw, or similar configuration could be utilized to engage the suture 16. Furthermore, the hook 30 is preferably a wire that is of sufficient rigidity to maintain its shape and overcome the outward radial force of the stent 10, while also having flexibility to be adaptable for a variety of vascular and nonvascular applications.

Thus, FIGS. 7 and 8 generally illustrate the positioning of the tube 26, pusher 28, and hook 30 prior to initiating the repositioning or removal of the stent 10. Thus, when the hook member 42 engages the suture 16, force applied by the hook 30 in the direction depicted by arrow 48 will cause the suture to purse string or draw down the proximal end of the stent 10. When the pusher 28 is moved downwardly depicted by arrow 46, the gripping member 38 will restrain the stent 10 to hold the stent in place while the hook 30 pulls on the suture 16 with the hooking member 42.

FIGS. 9a-d illustrate the various steps involved in repositioning or removing a stent 10 from a lumen. In FIG. 9a, the gripping member 38 of the pusher 28 is positioned to engage a proximal end of the stent 10, while the hook member 42 of the hook 30 engages a suture 16 also at the proximal end of the stent. As the pusher 28 is moved downwardly (arrow 46), the hook 30 pulls upwardly (arrow 48) on the suture 16 to purse string the suture, causing the proximal end of the stent to crimp or constrict in diameter, as shown in FIG. 9b. As the proximal end of the stent 10 is crimped, the tube 26 may be moved downwardly (arrow 50) such that the proximal end of the stent is positioned within the funnel-shaped end 34 of the tube (FIG. 9c). The tube 26 may be moved distally to surround only the proximal end of the stent 10, so that the leading edge of the stent in the removal direction cannot engage the lumen or other tissue. The tube 26 may also be moved distally so as to completely surround the stent 10 so that no portion of the stent can drag on the lumen interior wall when the stent is removed. Thereafter, the tube 26, pusher 38, and hook 30 are moved concurrently (arrows 48, 52, 54) to remove or reposition the stent 10, as depicted in FIG. 9d. As described above, the pusher 28 may also be positioned at the distal end of the stent 10 such that the gripping member 38 engages a suture 16 at the distal end of the stent while the hook 30 crimps the proximal end of the stent. The remaining steps for removing or repositioning the stent 10 would be carried out in the same manner as described above. Once the removal device 24 releases the suture 16, the proximal or distal end of the stent 10 will expand to its original diameter.

Therefore, the removal device 24 is capable of repositioning or removing a stent 10 from a lumen while reducing the incidence of damage to the lumen or the stent. As such, the removal device 24 may crimp the stent 10 inside of the tube 26 and then remove the stent rather than removing the stent in its deployed state, i.e., without crimping. The removal device 24 is easily deployed within the lumen and proximate to the implanted stent 10 such that the removal device is capable of being used for various vascular and nonvascular applications.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A stent removal device for removing or repositioning a stent within a lumen, the stent comprising an element arranged circumferentially about an entire circumference of the stent to produce a purse-string effect to reduce a diameter of the stent when the element is pulled in a proximal direction, the stent removal device comprising:
    a tube having an elongate cylindrical body with a proximal end and a distal end configured to be positioned within the lumen proximate to the stent, wherein the tube is configured to receive at least a portion of the stent therein;
    a pusher having a longitudinal portion and a gripping member, the longitudinal portion of the pusher configured to be positioned within and extend through a channel of the tube and the gripping member coupled to a distal end of the longitudinal portion of the pusher and configured to extend laterally and distally on both an inner side and an outer side of an edge of the stent to engage and restrain the edge of the stent, wherein the longitudinal portion is sufficiently rigid to restrain proximal movement of the stent while the pusher applies a force distally; wherein the pusher is configured to be positioned through the stent while the tube is positioned proximal of the stent; and
    a hook having a single unbranched longitudinal portion and a hook member, the single unbranched longitudinal portion of the hook configured to be positioned within and extend through the channel of the tube alongside the longitudinal portion of the pusher, the hook member coupled to a distal end of the single unbranched longitudinal portion of the hook and configured to engage the element such that a force in the proximal direction applied to the hook causes the stent to purse string, the hook member including a ridge that extends proximally to secure the element to prevent the element from disengaging from the hook member during application of the force in the proximal direction,
    wherein the pusher and hook are independently operable and the pusher is configured to, during operation, engage the edge of the stent either proximal or distal to the hook as the hook engages the element of the stent.

2. The stent removal device according to claim 1, wherein the tube comprises a funnel-shaped end that is configured to receive at least at portion of the stent and retain the stent therein.

3. The stent removal device according to claim 1, wherein longitudinal portion of the pusher has flexibility to be adaptable to a variety of vascular and nonvascular applications.

4. The stent removal device according to claim 1, wherein the gripping member is configured to engage the element or an edge of an opening defined in the stent at a proximal end of the stent.

5. The stent removal device according to claim 1, wherein the longitudinal portion of the pusher is capable of extending within the stent, and wherein the gripping member is capable of engaging the element proximate to a distal end of the stent.

6. The stent removal device according to claim 1, wherein the longitudinal portion of the hook comprises a wire.

7. The stent removal device according to claim 1, wherein the hook member is configured to partially encircle the element.

8. The stent removal device according to claim 1, wherein the longitudinal portion of the pusher is disposed lateral to and external to the longitudinal portion of the hook, and
    wherein the longitudinal portion of the hook is disposed lateral to and external to the longitudinal portion of the pusher.

9. The stent removal device according to claim 1, wherein the longitudinal portion of the pusher comprises a solid wire, and wherein the longitudinal portion of the hook comprises a solid wire.

10. The stent removal device according to claim 1, wherein an exterior surface of the longitudinal portion of the pusher is disposed adjacent and alongside an exterior surface of the longitudinal portion of the hook.

11. A stent removal device for removing or repositioning a stent within a lumen, the stent comprising at least one element arranged circumferentially thereabout to produce a purse-string effect to reduce a diameter of the stent when the element is pulled, the stent removal device comprising:
    a pusher comprising a longitudinal portion configured to be positioned within and extend through a channel of a tube along an entire length of the tube and comprising a gripping member configured to extend laterally and distally on both an inner side and an outer side of an edge of the stent to engage and restrain the edge of the stent, wherein the pusher is configured to be positioned through the stent while the tube is positioned proximal of the stent; and
    a hook comprising a single unbranched longitudinal portion and a hook member, wherein the single unbranched longitudinal portion is configured to extend proximally from the hook member to be positioned within and extend through the channel of the tube along the entire length of the tube alongside the longitudinal portion of the pusher, and the hook member is configured to engage the element such that a proximal force applied to the hook causes the stent to purse string, the hook member including a ridge that extends proximally to secure the element to prevent the element from disengaging from the hook member during application of the proximal force,
    wherein the pusher and hook are independently operable and the pusher is configured to, during operation, engage the edge of the stent either proximal or distal to the hook as the hook engages the element of the stent.

12. The stent removal device according to claim 11, wherein the gripping member is configured to engage the element or an edge of an opening defined in the stent at a proximal end.

13. The stent removal device according to claim 11, wherein the gripping member is configured to engage the element proximate to a distal end of the stent.

14. The stent removal device according to claim 11, wherein the gripping member comprises one of a U-shape, a Y-shape, and a L-shape.

15. The stent removal device according to claim 14, wherein the hook member is configured to partially encircle the element.

16. The stent removal device according to claim 11, wherein the longitudinal portion of the pusher is disposed lateral to and external to the longitudinal portion of the hook, and
wherein the longitudinal portion of the hook is disposed lateral to and external to the longitudinal portion of the pusher.

17. The stent removal device according to claim 11, wherein the longitudinal portion of the pusher comprises a solid wire, and wherein the longitudinal portion of the hook comprises a solid wire.

18. The stent removal device according to claim 11, wherein an exterior surface of the longitudinal portion of the pusher is disposed adjacent and alongside an exterior surface of the longitudinal portion of the hook.

19. A stent removal device for removing or repositioning a stent within a lumen, the stent comprising at least one element arranged circumferentially about the stent to produce a purse-string effect to reduce a diameter of the stent when the element is pulled, the stent removal device comprising:
a pusher comprising a solid longitudinal portion formed by a wire configured to be positioned within and extend through a channel of a tube along an entire length of the tube and comprising a gripping member configured to engage an edge of the stent, wherein the gripping member is configured to extend laterally and distally on both an inner side and an outer side of the edge of the stent to engage and restrain the edge of the stent, wherein the pusher is configured to be positioned through the stent while the tube is positioned proximal of the stent; and a hook comprising a solid unbranched longitudinal portion formed by a wire and a hook member, wherein the unbranched longitudinal portion is configured to be positioned within and extend through the channel of the tube along the entire length of the tube alongside the longitudinal portion of the pusher to the hook member, wherein the hook member is configured to partially encircle and engage the element such that a force in the proximal direction applied to the hook causes the stent to purse string, the hook member including a ridge that extends proximally to secure the element to prevent the element from disengaging from the hook member during application of the force in the proximal direction, wherein, during operation, the pusher and hook are independently operable and the pusher is configured to engage the edge of the stent either proximal or distal to the hook as the hook engages the element of the stent.

20. The stent removal device according to claim 19, wherein the gripping member comprises one of a U-shape, a Y-shape, and a L-shape.

* * * * *